(12) United States Patent
Severgnini et al.

(10) Patent No.: US 11,642,083 B2
(45) Date of Patent: May 9, 2023

(54) EXTENDABLE BIOSENSING DEVICES AND VEHICLES INCORPORATING THE SAME

(71) Applicant: Toyota Motor Engineering & Manufacturing North America, Inc., Plano, TX (US)

(72) Inventors: Frederico Marcolino Quintao Severgnini, Ann Arbor, MI (US); Ercan Mehmet Dede, Ann Arbor, MI (US)

(73) Assignee: TOYOTA MOTOR ENGINEERING & MANUFACTURING NORTH AMERICA, INC., Plano, TX (US)

( * ) Notice: Subject to any disclaimer, the term of this patent is extended or adjusted under 35 U.S.C. 154(b) by 435 days.

(21) Appl. No.: 16/778,844

(22) Filed: Jan. 31, 2020

(65) Prior Publication Data

US 2021/0236061 A1     Aug. 5, 2021

(51) Int. Cl.
| | |
|---|---|
| *A61B 5/00* | (2006.01) |
| *A61B 5/01* | (2006.01) |
| *A61B 5/053* | (2021.01) |
| *B60N 2/75* | (2018.01) |
| *A61B 90/00* | (2016.01) |

(52) U.S. Cl.
CPC .......... *A61B 5/6843* (2013.01); *A61B 5/0059* (2013.01); *A61B 5/01* (2013.01); *A61B 5/053* (2013.01); *A61B 5/6824* (2013.01); *A61B 5/6831* (2013.01); *A61B 5/6893* (2013.01); *A61B 2090/064* (2016.02); *A61B 2562/164* (2013.01); *B60N 2/797* (2018.02)

(58) Field of Classification Search
None
See application file for complete search history.

(56) References Cited

U.S. PATENT DOCUMENTS

| | | | | |
|---|---|---|---|---|
| 5,069,219 | A * | 12/1991 | Knoblich | A61B 5/02233 600/492 |
| 5,853,005 | A | 12/1998 | Scanlon | |
| 8,721,557 | B2 | 5/2014 | Chen et al. | |
| 10,335,044 | B2 | 7/2019 | Banet et al. | |
| 2004/0041998 | A1* | 3/2004 | Haddad | G06V 40/1312 356/71 |
| 2008/0114218 | A1 | 5/2008 | Suyama et al. | |
| 2011/0021932 | A1* | 1/2011 | Kim | A61B 5/02233 600/499 |
| 2018/0348759 | A1* | 12/2018 | Freeman | A61B 5/021 |
| 2019/0083022 | A1 | 3/2019 | Huang | |

(Continued)

OTHER PUBLICATIONS

HapWRAP: Soft Growing Wearable Haptic Device (https://smartdevicess.createdsites.com) May 27, 2019.

(Continued)

*Primary Examiner* — Yi-Shan Yang
(74) *Attorney, Agent, or Firm* — Dinsmore & Shohl LLP

(57) ABSTRACT

An extendable biosensing device comprising a robotic structure. The robotic structure comprises a pliable exterior lining and an extendable core. The robotic structure comprises at least one sensor located on or within the pliable exterior lining. The sensor is configured to measure a physiological condition. The extendable core automatically extends from a retracted state to a deployed state in response to a triggering event.

20 Claims, 10 Drawing Sheets

(56) References Cited

U.S. PATENT DOCUMENTS

2021/0153754 A1* 5/2021 Ozawa ............... A61B 5/02108
2022/0031178 A1* 2/2022 Brulet ............... A61B 5/02233

OTHER PUBLICATIONS

Yilmaz, et al., Detecting Vital Signs with Wearable Wireless Sensors (https://ncbi.nlm.nih.gov/pmc/articles/PMC3231103/) Dec. 2, 2010; Multidisciplinary Digital Publishing Institute (MDPI).
Choi, et al., Highly conductive, stretchable and biocompatible Ag-Au core-sheath nanowire composite for wearable and implantable bioelectronics; Nature Nanotechnology, vol. 13, Nov. 2018, pp. 1048-1056.
Gao, et al., Wearable Microfluidic Diaphragm Pressure Sensor for Health and Tactile Touch Monitoring; Advanced Materials, 2017, 29, 1701985.
Kweon, et al., Wearable high-performance pressure sensors based on three-dimensional electrospun conductive nanofibers; NPG Asia Materials (2018), pp. 540-551.
Wang, et al., Monitoring of the central blood pressure waveform via a conformal ultrasonic device; Nature Biomedical Engineering, vol. 2; Sep. 2018; pp. 687-695.
Agharese, et al., HapWRAP: Soft Growing Wearable Haptic Device; 2018 IEEE International Conference on Robotics and Automation (ICRA), May 21-25, 2018; pp. 5466-5472.
Gao, et al., Fully integrated wearable sensor arrays for multiplexed in situ perspiration analysis; Nature, Jan. 28, 2016, vol. 529.

* cited by examiner

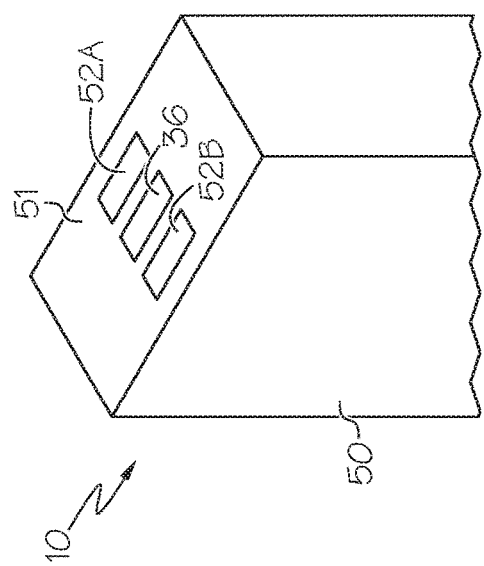
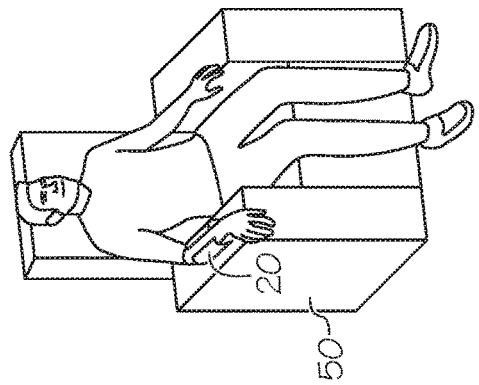
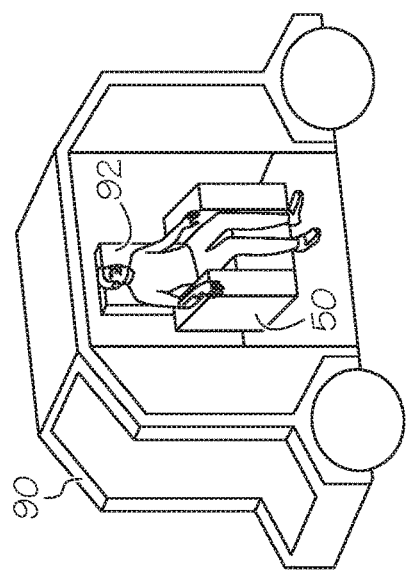
FIG. 7A
FIG. 7B
FIG. 7C

EXTENDABLE BIOSENSING DEVICES AND VEHICLES INCORPORATING THE SAME

BACKGROUND

Field

The present specification generally relates to biosensing devices, and more specifically, to pliable biosensing devices that may automatically deploy to detect a user's physiological conditions.

Technical Background

Biosensing devices can be used to measure a variety of vital signs or physiological conditions of a user. A first primary set of biosensing devices come in the form of large, heavy machinery. These biosensing devices are often deployed in hospitals, for instance, to detect patient physiological conditions. A second primary set of biosensing devices may be small and transportable, but require users to deploy the biosensing devices themselves. These biosensing devices may come in the form of smart watches that can measure a user's heartrate, for instance. Users must deliberately attach these biosensing devices to themselves.

Accordingly, a need exists for alternative biosensing devices that may automatically deploy to detect a user's physiological conditions.

SUMMARY

In one embodiment, an extendable biosensing device includes a robotic structure. The robotic structure includes a pliable exterior lining and an extendable core. The robotic structure includes at least one sensor located on or within the pliable exterior lining. The at least one sensor is configured to measure a physiological condition of a user. The extendable core of the robotic structure automatically extends from a retracted state to a deployed state in response to a triggering event.

In another embodiment, an extendable biosensing device includes a robotic structure. The robotic structure includes a pliable exterior lining and an extendable core. The robotic structure includes at least one flexible sensor located on or within the pliable exterior lining. The at least one flexible sensor is configured to measure a physiological condition of a user. The extendable core of the robotic structure automatically extends from a retracted state to a deployed state in response to a triggering event, and the extendable core automatically retracts when a triggering event expires. In a retracted state, the extendable core is concealed within a housing. In a deployed state, the robotic structure is optimally configured to wrap itself around a body part of the user. The housing which conceals the robotic structure in a retracted state is on or within an interior member of a mobile transport.

In yet another embodiment, a vehicle that includes a motor, two wheels, a seat, and an extendable biosensing device is provided. The extendable biosensing device includes a robotic structure. The robotic structure includes a pliable exterior lining and an extendable core. The robotic structure includes at least one flexible sensor located on or within the pliable exterior lining. The at least one flexible sensor is configured to measure a physiological condition of a user. The extendable core of the robotic structure extends from a retracted state to a deployed state in response to a triggering event, and the extendable core automatically retracts when a triggering event expires. In a retracted state, the extendable core is concealed within a housing. In a deployed state, the robotic structure is optimally configured to wrap itself around a body part of the user.

These and additional objects and advantages provided by the embodiments described herein will be more fully understood in view of the following detailed description, in conjunction with the drawings.

BRIEF DESCRIPTION OF THE DRAWINGS

The embodiments set forth in the drawings are illustrative and exemplary in nature and not intended to limit the subject matter defined by the claims. The following detailed description of the illustrative embodiments can be understood when read in conjunction with the following drawings, where like structure is indicated with like reference numerals and in which:

FIG. 7A schematically depicts an embodiment of a mobile transport including an extendable biosensing device according to one or more embodiments shown or described herein;

FIG. 7B schematically depicts the housing of the extendable biosensing device of the embodiment of FIG. 7A according to one or more embodiments shown or described herein;

FIG. 7C schematically depicts the embodiment of FIG. 7A with the extendable biosensing device in a deployed state according to one or more embodiments show or described herein;

DETAILED DESCRIPTION

Embodiments described herein are generally directed to an extendable biosensing device. The extendable biosensing device may include a robotic structure. The robotic structure may include a pliable exterior lining and an extendable core. The robotic structure may include at least one sensor located on or within the pliable exterior lining. The at least one sensor may be configured to measure a physiological condition of a user. The extendable core, and along with it, the robotic structure, automatically extend from a retracted state to a deployed state in response to a triggering event.

Figure 1A:
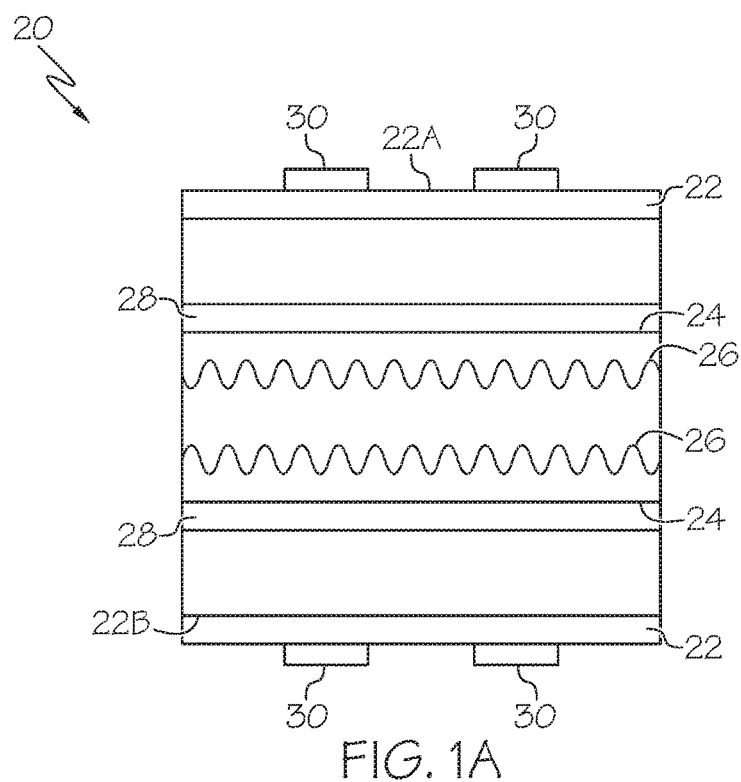
FIG. 1A schematically depicts a cross-section of an illustrative embodiment of a robotic structure having extendable elements in a retracted state according to one or more embodiments shown or described herein.
Figure 1B:
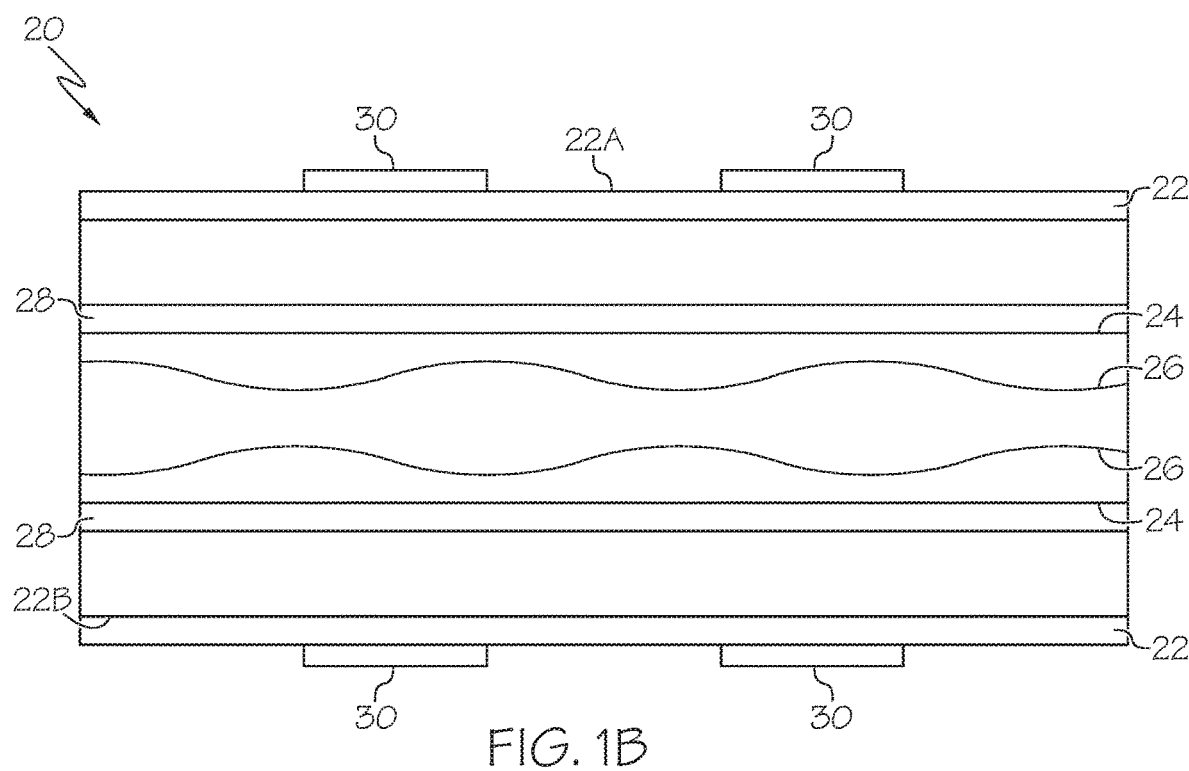
FIG. 1B schematically depicts the embodiment of FIG. 1A having extendable elements in a deployed state according to one or more embodiments shown or described herein.

Referring initially to FIGS. 1A and 1B, a schematic depiction of an example robotic structure 20, which forms a portion of an extendable biosensing device 10 (FIG. 4A-6F), is depicted. FIGS. 1A and 1B depict a cross-sectional view of robotic structure 20. Robotic structure 20 may include pliable exterior lining 22. Pliable exterior lining may include exterior edge 22A and interior edge 22B. Pliable exterior lining 22 may easily bend to shape itself around a contacting structure. For instance, pliable exterior lining 22 may deform to conform itself to different structural elements. These structural elements may have different cross sections, such as circular or square, for instance. These structural elements may also have different cross sectional areas. No matter the cross sectional shape or area of a structural element, pliable exterior lining 22 may be able to deform to closely fit the structural element. By closely fitting the structural element, pliable exterior lining 22 may directly abut the structural element, or in other words, leave no open space between pliable exterior lining 22 and the structural element. Pliable exterior lining 22 may also deform to conform itself to a variety of surface elements. For instance, whether the structural element includes a rough, coarse surface with many bumps, or a soft, fragile surface, pliable exterior lining 22 may directly abut the surface without causing any damage to pliable exterior lining 22 or the surface of the structural element. Pliable exterior lining 22 may be any suitable material such as a rubber or soft plastic.

Extendable biosensing device 10 may be used in a variety of scenarios. For example, extendable biosensing device 10 may be a health sensor that wraps around an arm of a user. In some examples, extendable biosensing device 10 may be implemented in a vehicle to wrap around an arm of a driver or passenger. By automatically deploying from a retracted state to a deployed state, extendable biosensing device 10 obviates the risk of a driver not attaching a biosensing device to herself when operating a vehicle. In its retracted state, extendable biosensing device 10 may be easily contained within a variety of housings or structures. Extendable biosensing device 10 may comfortably wrap itself around a body part of a user and provide the user with real-time feedback on her physiological conditions. For example, if the biosensing device 10 were operating on a driver of a vehicle, it may be able to warn the driver of a health crisis she may experience in the near future, allowing the driver enough time to pull the vehicle over and call an ambulance.

Robotic structure 20 of extendable biosensing device 10 may also include extendable core 24 and extendable elements 26. Extendable core 24 may be within the interior of robotic structure 20. Extendable core 24 may be surrounded on all sides by pliable exterior lining 22. In some embodiments, extendable core 24 may directly border the interior edge of pliable exterior lining 22. In other embodiments, there may be open air between extendable core 24 and pliable exterior lining 22. Extendable core 24 may be made of any suitable elastically deformable material and functions to locally contain one or more extendable elements 26. As extendable elements 26 extend, extendable core 24 extends with them, causing the remainder of robotic structure 20, including pliable exterior lining 22 to extend as well. As extendable elements 26 retract, extendable core 24 retracts with them, causing the remainder of robotic structure 20, including pliable exterior lining 22, to retract as well. In other embodiments, robotic structure 20 may not include extendable core 24. In these embodiments, extendable elements 26 may be inside the entire interior of robotic structure 20, filling most or all of the void inside the interior edge 22B of pliable exterior lining 22.

Robotic structure 20 of extendable biosensing device 10 may also include one or more extendable elements 26. One or more extendable elements 26 may be a variety of elements that extend based on one or more stimuli. For example, one or more extendable elements 26 may be elastomers. Nematic elastomers, for instance, contain randomly oriented polymeric chains at high temperatures. Once the temperature drops below a critical temperature, the randomly oriented chains may align themselves, resulting in an overall deformation or extension of the elastomer. Nematic elastomers may undergo similar deformations in the presence or absence of light. Certain elastomers may also undergo similar deformations in the presence or absence of electricity. In another embodiment, one or more extendable elements 26 may be shape-memory alloys. Shape memory alloys take an original shape or configuration, and can deform by either bending or stretching when the shape-memory alloy is below its transition temperature. When heat is again applied to the shape-memory alloy and its temperature exceeds its transition temperature, the shape memory alloy returns to its original shape. Extendable elements 26 as shape-memory alloys may stretch and extend, or bend and shrink, when cooled, for instance. Elastomers and shape memory alloys are merely examples of extendable elements 26, however, and any number of other suitable materials may be used for one or more extendable elements 26. For instance, extendable elements 26 may be polymers. Additionally, any number of stimuli may control the deformation of extendable elements 26 depending on the specific extendable elements 26 chosen for implementation. Extendable elements 26 may be sensitive to light, electricity, temperature, or any other suitable stimulus.

FIG. 1A depicts a cross-sectional view of robotic structure 20 of extendable biosensing device 10 when one or more extendable elements 26 are in a retracted state. If one or more extendable elements 26 were nematic elastomers, for instance, FIG. 1A may depict the nematic elastomers in an original, randomly oriented state. As the nematic elastomers cool for instance, they may align and stretch, causing extendable core 24 and robotic structure 20 to extend, as depicted in FIG. 1B. As the temperature of the nematic elastomers rises again, robotic structure 20 may transition from the configuration depicted in FIG. 1B and return to the configuration depicted in FIG. 1A.

If shape-memory alloy were used as extendable elements 26, for example, the original shape of the shape-memory alloy may be that depicted in FIG. 1A or FIG. 1B. For instance, in one embodiment, the original shape of the shape-memory alloy may be the extended, deployed configuration in FIG. 1B. As the shape-memory alloy drops below a certain temperature, it may deform and bend, taking the shape depicted in FIG. 1A. The shape-memory alloy may be actively cooled in order for this transition to take place. In another embodiment, the transition temperature of the shape-memory alloy may be above standard room temperatures. Therefore, the shape-memory alloy may regularly be in its deformed, retracted state depicted in FIG. 1A in room temperature and return to its original extended state depicted in FIG. 1B upon application of heat to the shape-memory alloy. In another embodiment, the original shape of the shape-memory alloy may be the deformed, retracted configuration in FIG. 1A. As the shape-memory alloy drops below a certain temperature, it may deform and stretch, taking the shape depicted in FIG. 1B. The shape-memory alloy may be actively cooled in order for this transition to take place. In another embodiment, the transition temperature of the shape-memory alloy may be above standard room temperatures. Therefore, the shape-memory alloy may regularly be in its deformed, extended state depicted in FIG. 1B at room temperature and return to its original retracted state depicted in FIG. 1A by the application of heat to the shape-memory alloy.

Figure 2A:
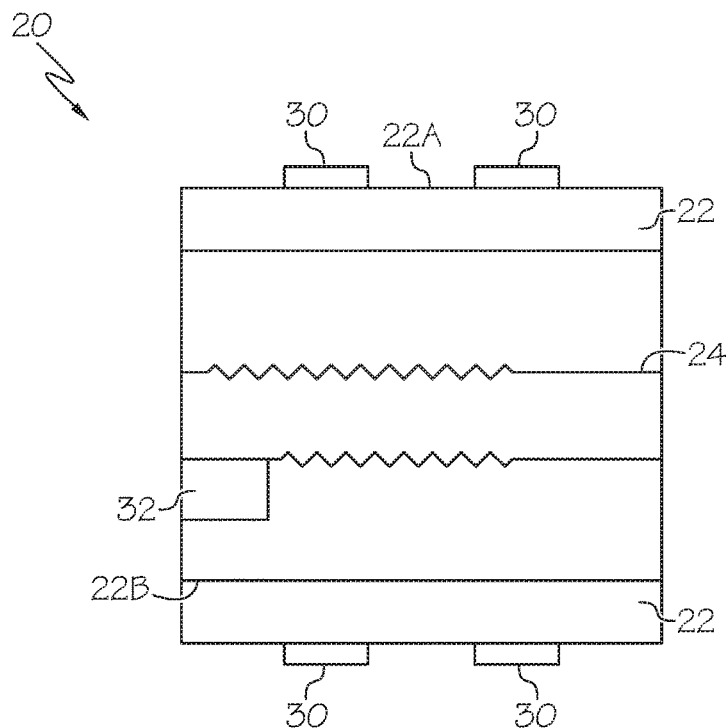
FIG. 2A schematically depicts a cross-section of an illustrative embodiment of a robotic structure having a pneumatic system in a retracted state according to one or more embodiments shown or described herein.
Figure 2B:
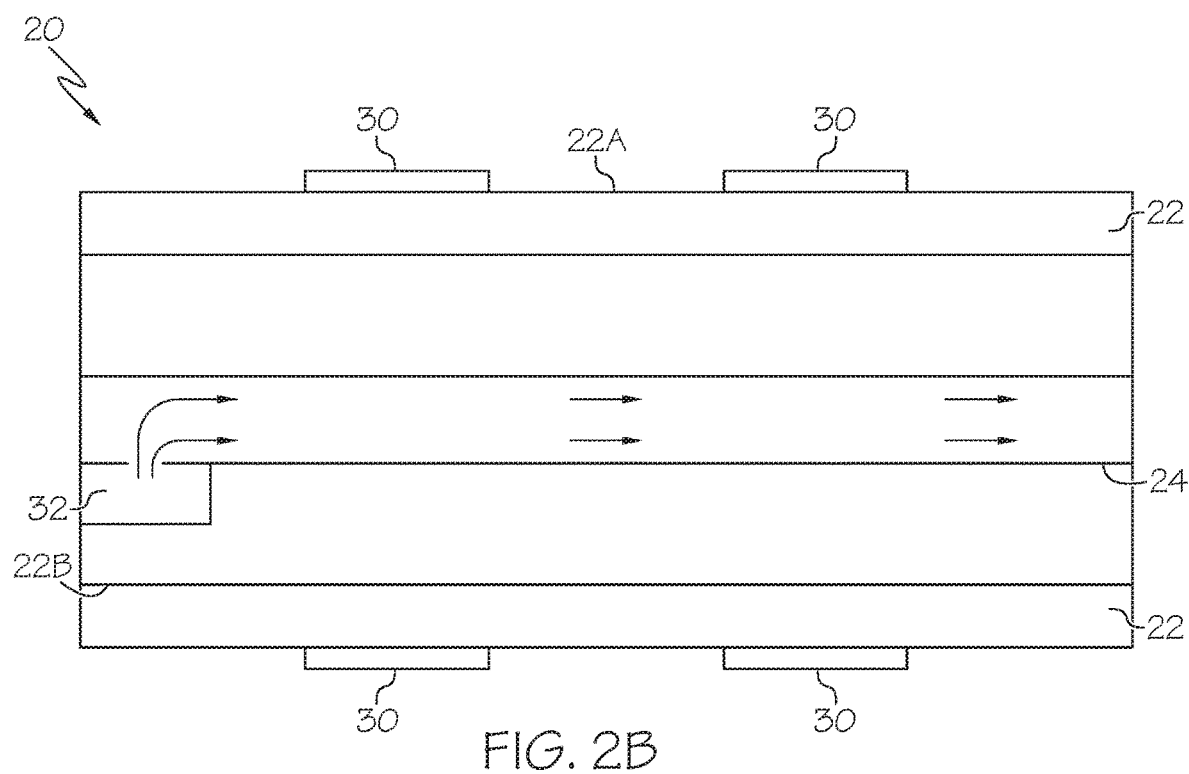
FIG. 2B schematically depicts the embodiment of FIG. 2A in a deployed state according to one or more embodiments shown or described herein.

Referring to FIGS. 2A and 2B, in an example alternative embodiment, robotic structure 20 of extendable biosensing device 10 may include a pneumatic system 32. Pneumatic system 32 may be operatively connected to extendable core 24. Pneumatic system 32 may supply air to extendable core 24, causing extendable core 24 to transition from a retracted state depicted in FIG. 2A to an extended, deployed state in FIG. 2B. Pneumatic system 32 may supply air to extendable core at a constant rate until robotic structure 20 reaches a desired or maximum internal pressure. Robotic structure 20 may include a valve or other release that selectively allows air out of robotic structure 20 to return to the retracted state depicted in FIG. 2A. In alternative embodiments, robotic structure 20 may not include extendable core 24. Therefore pneumatic system 32 may be operatively connected to robotic structure 20 at any point between interior edge 22B of pliable exterior lining 22.

Figure 3A:
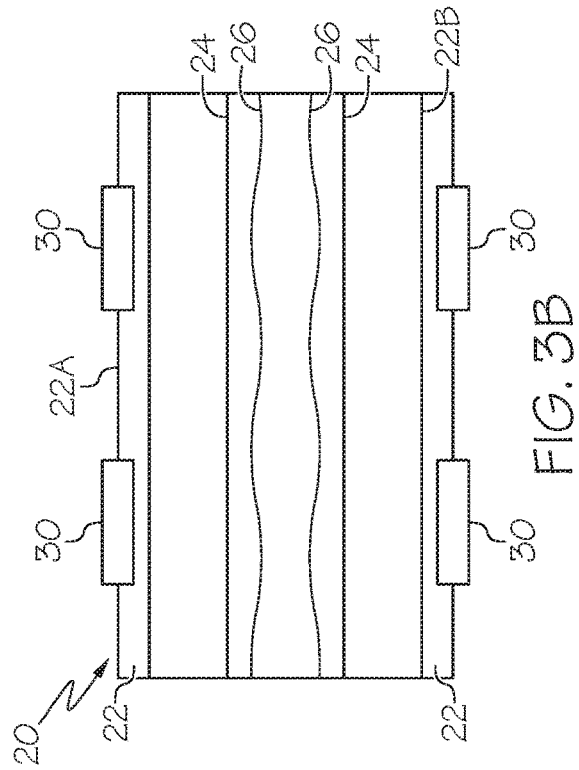
FIG. 3A schematically depicts a cross-section of an illustrative embodiment of a robotic structure having flexible sensors according to one or more embodiments show or described herein.
Figure 3B:
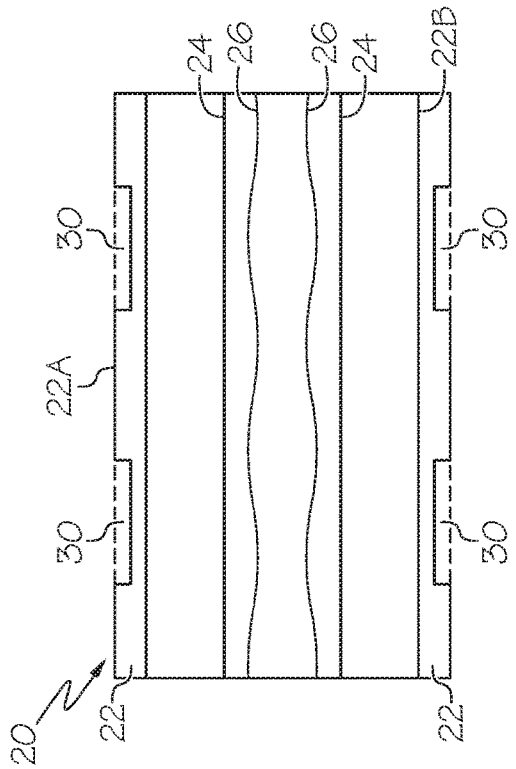
FIG. 3B schematically depicts a cross-section of an illustrative embodiment of a robotic structure having flexible sensors according to one or more embodiments show or described herein.
Figure 3C:
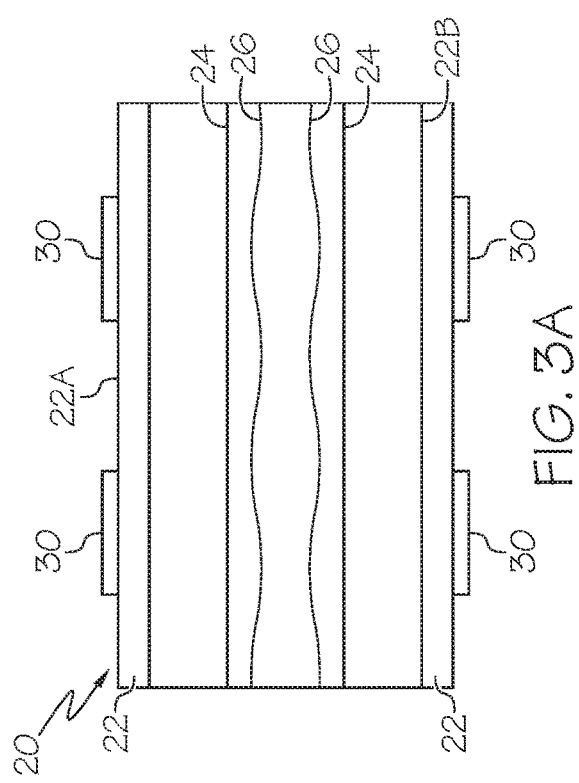
FIG. 3C schematically depicts a cross-section of an illustrative embodiment of a robotic structure having flexible sensors according to one or more embodiments show or described herein.
Figure 3D:
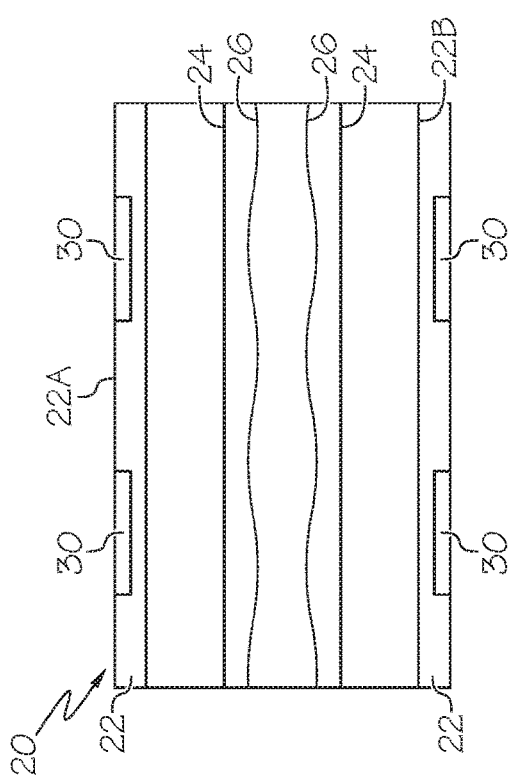
FIG. 3D schematically depicts a cross-section of an illustrative embodiment of a robotic structure having flexible sensors according to one or more embodiments show or described herein.

Now referring to FIGS. 3A-3D, a schematic depiction of an example robotic structure 20 is depicted. Robotic structure 20 of extendable biosensing device 10 may contain flexible sensors 30 in a variety of optimal arrangements. Referring first to FIG. 3A, flexible sensors 30 may be attached to exterior edge 22A of pliable exterior lining 22. Flexible sensors 30 may be fixed to exterior edge 22A with adhesives or any other suitable fixation. Referring now to FIG. 3B, flexible sensors 30 may be partially disposed within pliable exterior lining 22. A first portion of flexible sensors 30 may extend beyond exterior edge 22A of pliable exterior lining 22. A second portion of flexible sensors 30 may extend beneath exterior edge 22A of pliable exterior lining 22 and terminate between exterior edge 22A and interior edge 22B of pliable exterior lining 22. Now referring to FIG. 3C, flexible sensors 30 may be entirely enclosed within pliable exterior lining 22. Flexible sensors 30 may be attached to the interior side of external edge 22A via adhesive or any other suitable fixation. Referring now to FIG. 3D, flexible sensors 30 may be entirely disposed within pliable exterior lining 22 and exposed through openings in exterior edge 22A of pliable exterior lining 22. The width of flexible sensors 30 may be entirely disposed between exterior edge 22A and interior edge 22B of pliable exterior lining 22. There may be absences in exterior edge 22A that allow for a first surface of flexible sensors 30 to directly contact a user. Any one or any combination of sensor deployments depicted in FIGS. 3A-3D may be utilized in a single extendable biosensing device 10. The specific configuration selected may depend on the particular physiological condition that an individual flexible sensor 30 is designed to detect. For instance, some but not all flexible sensors 30 may be able to properly function with the exterior edge 22A of pliable exterior lining 22 between flexible sensors 30 and the user, as depicted in FIG. 3C. It should also be appreciated that in some embodiments, flexible sensors 30 are ultrathin. Therefore, the distinctions between sensor attachments depicted in FIGS. 3A, 3B, and 3D may not be readily apparent to the naked eye.

Flexible sensors 30 may be able to detect or measure a variety of physiological conditions. For instance, flexible sensors 30 may include stretchable, conductive nanocomposites that may function as electrodes necessary for ECG measurement. Flexible sensors 30 may include wireless nanofiber-based blood pressure sensors. Flexible sensors 30 may include ultrathin ultrasound devices that may determine blood pressure waveform. Flexible sensors 30 may include pressure sensors. Flexible sensors 30 may include sweat sensors that may detect blood glucose, dehydration, blood flow, and alcohol consumption. This list is merely exemplary, however, and is not meant to be limiting. It should be appreciated that any flexible sensor calibrated to measure a physiological condition may be used in conjunction with biosensing device 10.

In some embodiments, robotic structure 20 of extendable biosensing device 10 automatically extends from a retracted state depicted in FIGS. 1A and 2A to a deployed state depicted in FIGS. 1B and 2B. By automatic deployment or extension it is meant that robotic structure 20 may deploy without specific user instructions to do so. Robotic structure 20 may automatically extend in response to one or more triggering event. For instance, in preferred embodiments, robotic structure 20 may automatically extend from a retracted state when a triggering event signals that a user is optimally positioned to have their physiological conditions measured by extendable biosensing device 10. Extendable biosensing device 10 may recognize the triggering event with one or more sensing device 36. Sensing device 36 may be optimally positioned to detect the triggering event. Sensing device 36 may be a visual sensor, such as a camera. The visual sensor may detect when a user or a particular body part of the user is optimally positioned to receive robotic structure 20. In other embodiments, sensing device 36 may be a capacitive sensor. The capacitive sensor may be positioned to contact and detect the skin of a body part of the user that is optimally positioned to receive robotic structure 20. In yet another embodiment, sensing device 36 may be a temperature sensor. The temperature sensor may be configured to detect when an object having the normal body temperature of a human is optimally positioned to receive robotic structure 20. In yet another embodiment, sensing device 36 may be a force sensor. The force sensor may be configured to detect when a force is rested on a certain area of extendable biosensing device 10, indicating a body part of the user is optimally positioned to receive robotic structure 20. These sensors are merely exemplary, however. Any sensor that can measure a physical presence may be used as sensing device 36. The visual sensor, capacitive sensor, temperature sensor, and force sensor, for instance, may be used individually or in any combination with each other. While automatic deployment is primarily discussed herein, it should be appreciated that a user may be able to extend robotic structure 20 from a retracted state to a deployed state and vice versa with specific instructions delivers via a button, switch, or other user interface.

Figure 4B:
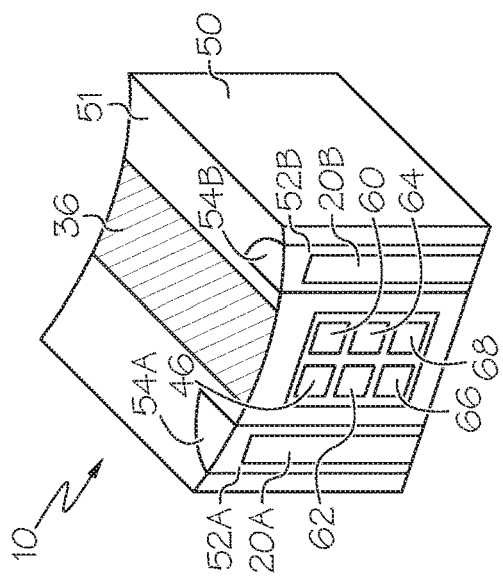
FIG. 4B schematically depicts an illustrative cross-section of the embodiment FIG. 4A having housing wells according to one or more embodiments shown or described herein.
Figure 4C:
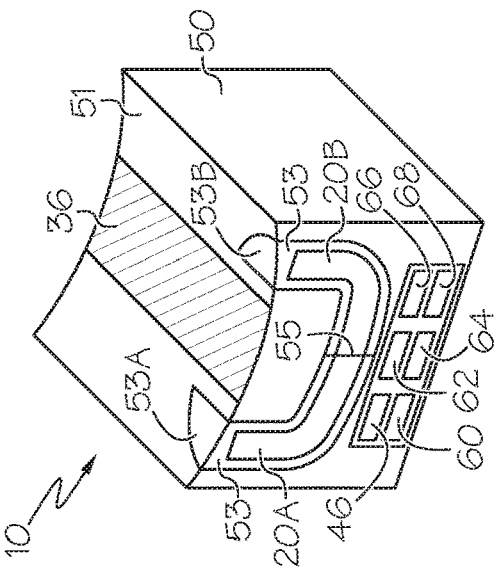
FIG. 4C schematically depicts an illustrative cross-section of the embodiment FIG. 4A having a housing canal according to one or more embodiments shown or described herein.
Figure 4A:
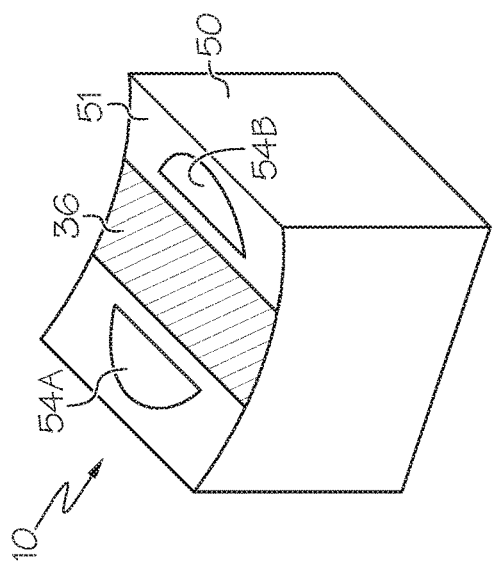
FIG. 4A schematically depicts an embodiment of an extendable biosensing device according to one or more embodiments shown or described herein.

Referring now to FIGS. 4A-4C, a schematic depiction of example embodiments of extendable biosensing device 10 is depicted. In some embodiments, extendable biosensing device 10 may include a housing 50. Housing 50 may be configured to house and conceal robotic structure 20, and extendable core 24 within, when in a retracted state. Housing 50 may contain at least one housing well 52 which allows for storage of robotic structure 20 in a retracted state and passage of robotic structure 20 as it extends to a deployed state. Housing well 52 may be a cavity of various sizes and shapes. Housing well 52 may terminate at an edge of housing 50 or within the interior of housing 50. Housing well opening 54 may allow for robotic structure 20 to extend outside housing 50. The remainder of housing 50 besides housing well 52 may be solid. In other embodiments, housing 50 may contain additional hollow portion to contain elements such as, but not limited to, a transceiver 60, a transmitter 62, a receiver 64, a microprocessor 66, a power source 68, or any other desirable element. Housing 50 may exist independently of any other objects. In other embodiments, housing 50 may be contained within other objects such as chairs, armrests, or any other object. The top of the object may include a cutout, resulting in the top surface 51 of housing 50 being the only portion of housing 50 exposed.

Referring now to FIGS. 4A-4E, in view of the previous figures already discussed, a schematic depiction of an example operation of extendable biosensing device 10 is depicted. Sensing device 36 may be attached to housing 50 of extendable biosensing device 10. In an alternative embodiment, sensing device 36 may be separate from housing 50. Sensing device 36 detects a triggering event, such as a body part of the user optimally positioned to receive robotic structure 20. Sensing device 36 may be operatively connected to robotic structure 20. Upon recognizing a force, temperature, or other triggering event as discussed above, sensing device 36 may convert physical measurements into electrical signals. Sensing device 36 may be operatively connected to robotic structure 20 through a wired connection. In another embodiment, sensing device 36 may be operatively connected to transmitter 62 which may be in wireless communication with robotic structure 20. Robotic structure 20 may be operatively connected to receiver 64 configured to receive the signal from sensing device 36 and transmitter 62. In another embodiment, sensing device 36 may be operatively connected to microprocessor 66. Microprocessor 66 may determine whether a signal collected from one or more sensing device 36 constitutes a triggering event or not. Microprocessor 66 may collect various quantities from one or more sensing device 36 and determine if the quantities are indicative of a human or human body part. If microprocessor 66 determines the information collected by sensing device 36 is not indicative of a human body part being optimally positioned to receive robotic structure 20, microprocessor 66 may not instruct transmitter 62 to send a signal to receiver 64. In an alternative embodiment, robotic structure 20 may be operatively connected to microprocessor 66. In this embodiment, transmitter 62 of sensing device 36 may send all detected signals to receiver 64. Microprocessor 66 in communication with receiver 64 may determine whether the signal indicates a triggering event, and instruct robotic structure 20 to deploy in the event a triggering event is detected.

Once the triggering event is detected, robotic structure 20 automatically extends from a retracted state to a deployed state. Referring now to FIGS. 1A-2B, the automatic extension and deployment of robotic structure 20 will be discussed in greater detail. Specifically, referring to FIGS. 1A and 1B robotic structure 20 including extendable elements 26 is depicted. Upon sensing device 36 sensing a triggering event, such as a body part being optimally positioned to receive robotic structure 20, an electrical signal to deploy is sent from sensing device 36 to robotic structure 20 through wired or wireless means, as discussed above. Once robotic structure 20 receives the signal, extendable biosensing device 10 may begin to operate extendable element control 28. For instance, when extendable elements 26 include shape-memory alloys, for instance, extendable element control 28 may be any suitable heating or cooling element. Extendable element control 28 may fully surround extendable core 24, heating or cooling extendable elements 26 within. In response to the heating or cooling, extendable elements 26 may extend, causing robotic structure 20 to fully deploy. Pliable exterior lining 22 may insulate robotic structure 20. Therefore, even in a deployed state, when the interior of robotic structure 20 is being heated or cooled, a user may not feel the internal temperature mechanisms through pliable exterior lining 22. Extendable element control 28 may be any suitable structure or mechanism depending on the particular extendable elements 26 incorporated in extendable biosensing device 10. Extendable element control 28 may include one or more light or electricity sources directed at extendable core 24 and extendable element 26 within to influence particular elastomers or polymers, for instance.

Specifically referring to FIGS. 2A and 2B, robotic structure 20 including pneumatic system 32 is depicted. Upon sensing device 36 sensing a triggering event, such as a body part being optimally positioned to receive robotic structure 20, an electrical signal to deploy is sent from sensing device 36 to robotic structure 20 through wired or wireless means, as discussed above. Once robotic structure 20 receives the signal, extendable biosensing device 10 may begin to operate pneumatic system 32. For instance, pneumatic system 32 may begin to provide air into extendable core 24 at a predetermined rate. As extendable core 24 expands, the remainder of robotic structure 20 expands with it.

Robotic structure 20 may also return from the extended deployed state depicted in FIGS. 1B and 2B to the retracted state depicted in FIGS. 1A and 2A. For instance, once a triggering event expires, this may be communicated from sensing device 36 to robotic structure 20 through wired or wireless communication in the same manner the detection of a triggering event is communicated from sensing device 36 to robotic structure 20, as discussed above. The expiration of the triggering event may be sensing device 36 detecting a body part of a user is no longer optimally positioned to receive robotic structure 20. For instance, if a user were to remove his or her arm from robotic structure 20 of extendable biosensing device 10, as will be discussed below, sensing device 36 may determine that the arm of the user is no longer in a position to receive robotic structure 20. Once this signal is sent to robotic structure 20, robotic structure 20 may actively retract or passively retract. Robotic structure 20 may be able to quickly retract through active retraction. For instance, with respect to FIGS. 1A and 1B, if robotic structure 20 extended from a retracted state to a deployed state by applying heat to extendable elements 26 through extendable element control 28, robotic structure 20 may actively retract by cooling extendable elements 26 through element control 28. In another embodiment, robotic structure may passively retract. For instance, instead of actively cooling extendable elements 26, robotic structure 20 may simply stop supplying heat to extendable elements 26 through extendable element control 28. In this case, extendable elements 26 would naturally dissipate heat and eventually return to their retracted state. Now with respect to FIGS. 2A and 2B, if robotic structure 20 extended from a deployed state by pneumatic system 32 pumping air into extendable core 24, robotic structure 20 may actively retract by activating a valve and releasing air from extendable core 24. In another embodiment, robotic structure 20 may passively retract when pneumatic system 32 stops supplying air to extendable core 24, and extendable core 24 slowly releases air over time.

Figure 4E:
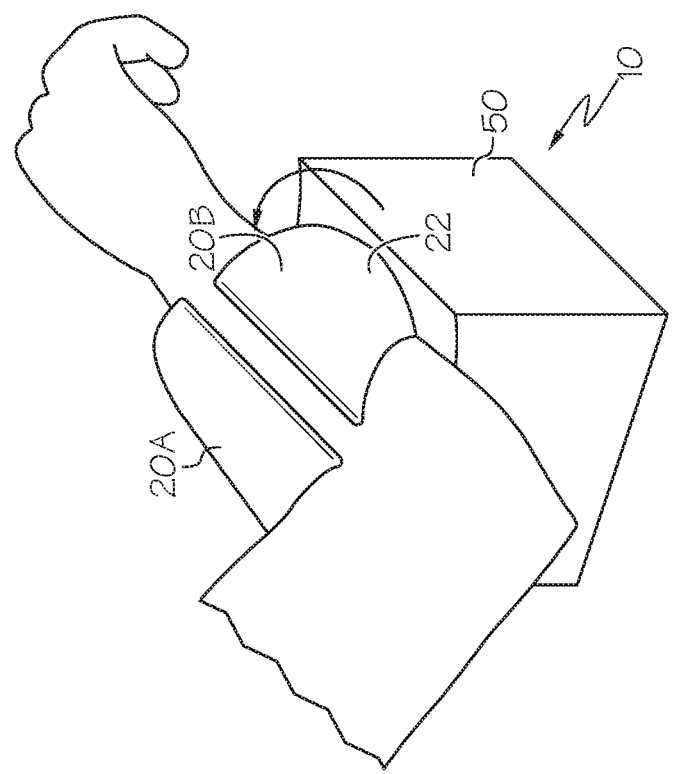
FIG. 4E schematically depicts the embodiment of FIG. 4D with the extendable biosensing device in a deployed state according to one or more embodiments shown or described herein.
Figure 4D:
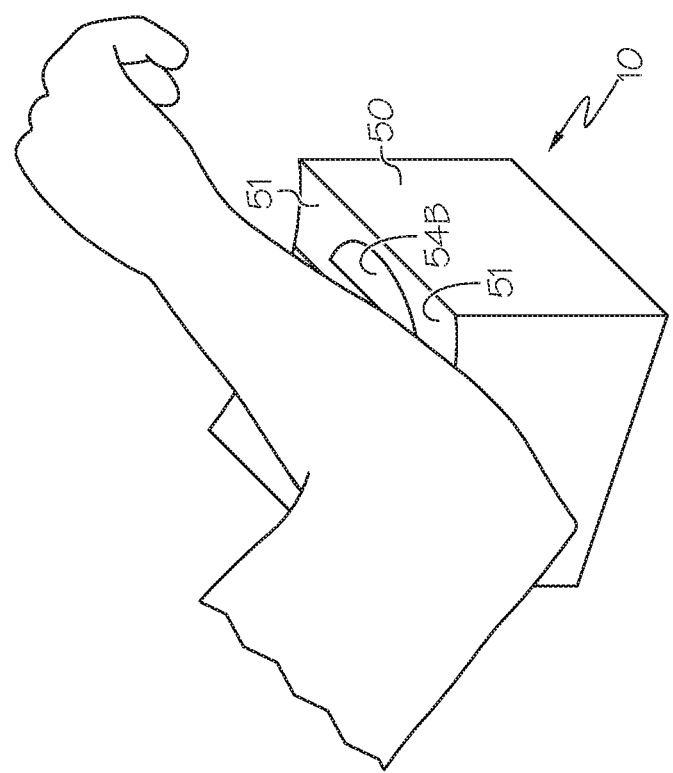
FIG. 4D schematically depicts the embodiment of FIG. 4A with a body part on the extendable biosensing device according to one or more embodiments shown or described herein.

Different deployed configurations of robotic structure 20 of extendable biosensing device 10 will now be discussed. Specifically referring to FIGS. 4A-4E, an embodiment of extendable biosensing device 10 may include a first robotic structure 20A and a second robotic structure 20B. Referring now to FIG. 4B, first robotic structure 20A and second robotic structure 20B may be contained in first housing well 52A and second housing well 52B, respectively. First and second housing wells 52A and 52B may be operatively arranged and sized to both contain first and second robotic structures 20A and 20B, respectively, in retracted states. First and second housing wells 52A and 52B may be operatively arranged and sized to allow passage of first robotic structure 20A and second robotic structure 20B, respectively, as they begin to extend and deploy. First and second robotic structures 20A and 20B may be fixedly secured to the bottom of housing wells 52A and 52B, respectively, ensuring that first and second robotic structures 20A and 20B do not detach from housing 50 when extending or in operation. Referring now to FIGS. 4D and 4E, as extendable biosensing device 10 extends, first robotic structure 20A and second robotic structure 20B deploy from housing well openings 54A and 54B, respectively, and contact a body part of a user optimally positioned to receive robotic structures 20A and 20B. One of first robotic structure 20A and second robotic structure 20B may approach the body part from the lateral edge of the body part. The other of first robotic structure 20A and second robotic structure 20B may approach the body part from the medial edge of the body part. First robotic structure 20A and second robotic structure 20B may form a partial cuff around the body part of a user. Therefore, a portion of the body part of the user remains uncontacted by any of first robotic structure 20A, second robotic structure 20B, sensing device 36, or housing 50. The sum of the circumferential distances of first robotic structure 20A and second robotic structure 20B around the body part of the user is less than the circumference of the body part of the user. First robotic structure 20A and second robotic structure 20B may include flexible sensors 30 around their entire circumferences, or first robotic structure 20A and second robotic structure 20B may only contain flexible sensors 30 on the circumferential portions facing sensing device 36, where a user is expected to rest a body part.

Referring now to FIG. 4C, first robotic structure 20A and second robotic structure 20B may be contained in housing canal 53. Housing canal 53 may be operatively arranged and sized to both contain first and second robotic structures 20A and 20B in retracted states and to allow passage of robotic structures 20A and 20B therethrough as robotic structures 20A and 20B begin to extend and deploy. First and second robotic structures 20A and 20B may be fixedly secured to a dividing wall 55 of housing canal 53, ensuring that first and second robotic structures 20A and 20B do not detach from housing 50 when extending or in operation. In another embodiment, robotic structures 20A and 20B are not fixedly secured to dividing wall 55. Instead, robotic structures 20A and 20B may be fixedly secured to an inner wall of housing canal 53. Referring now to FIGS. 4D and 4E, as extendable biosensing device 10 extends, first robotic structure 20A and second robotic structure 20B deploy from housing canal openings 53A and 53B, respectively, and contact a body part of a user optimally positioned to receive robotic structures 20A and 20B. One of first robotic structure 20A and second robotic structure 20B may approach the body part from the lateral edge of the body part. The other of first robotic structure 20A and second robotic structure 20B may approach the body part from the medial edge of the body part. First robotic structure 20A and second robotic structure 20B may form a partial cuff around the body part of the user. Therefore, a portion of the body part of the user remains uncontacted by any of first robotic structure 20A, second robotic structure 20B, sensing device 36, or housing 50. The sum of the circumferential distances of first robotic structure 20A and second robotic structure 20B around the body part of the user is less than the circumference of the body part of the user. First robotic structure 20A and second robotic structure 20B may include flexible sensors 30 around their entire circumferences, or first robotic structure 20A and second robotic structure 20B may only contain flexible sensors 30 on the circumferential portions facing sensing device 36, where a user is expected to rest a body part.

Referring now to FIGS. 4D and 4E, examples of the embodiments depicted in FIGS. 4A-4C may be seen in relation to a body part of a user. In FIG. 4D, a user may place his or her arm on or over sensing device 36. Upon detecting the triggering event, extendable biosensing device 10 extends and robotic portions 20A and 20B deploy as discussed above. As can be seen in FIG. 4E, extendable biosensing device 10 conforms itself to a body part of the user. Specifically, pliable exterior lining 22 may conform to optimally fit a variety of body shapes. Depending on the specific size, shape, and characteristics of the body part, pliable exterior lining 22 may take different shapes or configurations. Pliable exterior lining 22 may mold itself to directly fit or abut the body part. Therefore, there may be no open space between pliable exterior lining 22 and the body part. The partial cuff configurations discussed above can be seen in FIG. 4E. The partial cuff configuration allows users to easily remove their arms or other body part from extendable biosensing device 10. This may be an important aspect in certain implementations. For instance, if extendable biosensing device 10 were installed within a vehicle, drivers may need to withdraw their body part from biosensing device 10 in emergency situations. Robotic structures 20A and 20B may be molded to take roughly a certain shape in a deployed state. For instance, if shape-memory alloy were used as extendable elements 26, the shape-memory alloy may be created to remember a distinct shape when it extends. In one embodiment, that distinct shape may be a crescent moon or partial cuff shape. Therefore, robotic structures 20A and 20B may be molded to take a certain configuration, assisting pliable exterior lining 22 in directly fitting the body part of the user.

Figure 5B:
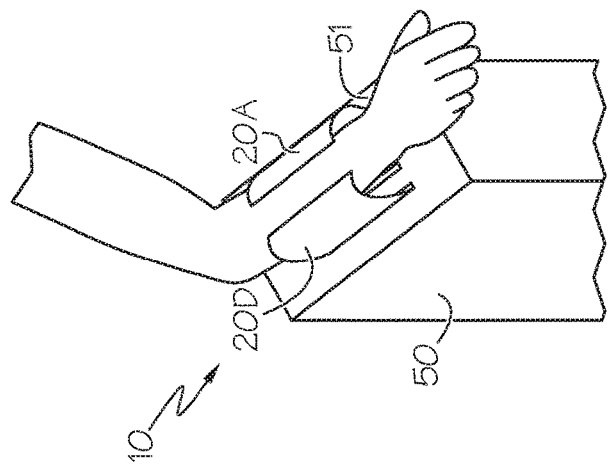
FIG. 5B schematically depicts the embodiment of FIG. 5A in a deployed state according to one or more embodiments shown or described herein.
Figure 5C:
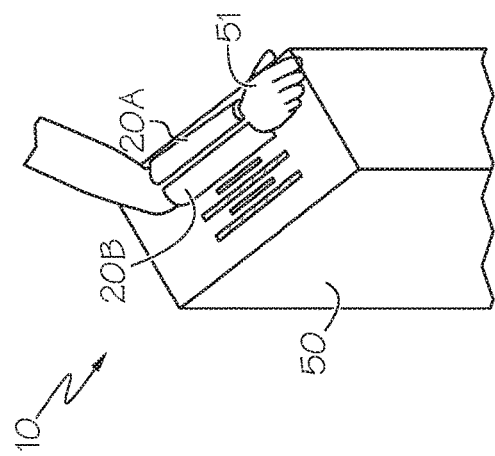
FIG. 5C schematically depicts the embodiment of FIG. 5A in a deployed state according to one or more embodiments shown or described herein.
Figure 5A:
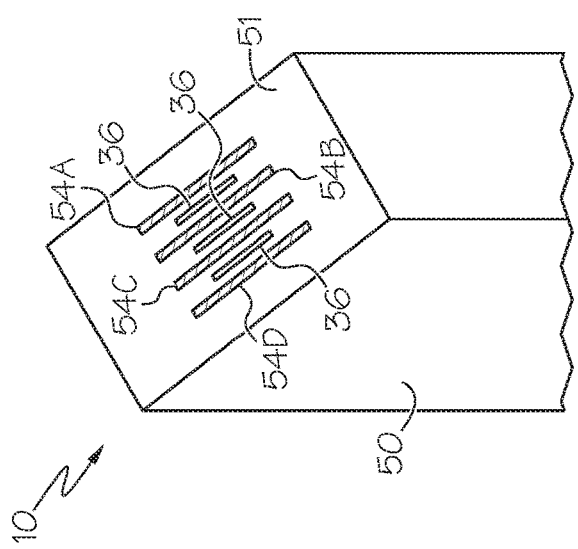
FIG. 5A schematically depicts an embodiment of an extendable biosensing device including multiple robotic structures according to one or more embodiments shown or described herein.

Another example embodiment of biosensing device 10 including a first robotic structure 20A and a second robotic structure 20B is depicted in FIG. 5A-5C. As discussed above, pliable exterior lining 22 may conform itself to body parts of various shapes. However, this is not without certain limitations, as there may be certain physical limits on the ability of robotic structure 20 to extend to certain lengths or widths. Additionally, there may be certain physical limits on the ability of pliable exterior lining 22 to elastically deform. Therefore, it may be difficult for extendable biosensing device 10, including a first robotic structure 20A and a second robot structure 20B, to fit both an arm of a young child and an arm of a large adult, for instance. Therefore, housing 50 may include more than two housing wells 52, and each housing well 52 may contain a separate robotic structure 20. As can be seen in FIGS. 5A-5C, housing 50 may include four housing wells, each corresponding to a housing well opening 54A-D. In addition to sensing a triggering event, sensing device 36 may also be configured to detect the width of a body part of a user. With reference to FIG. 5B, if a very large user were to place his or her arm, for instance, over housing 50 and sensing device 36, sensing device 36 may be able to detect that the arm extends roughly from housing well opening 54A to housing well opening 54D. Therefore, sensing device 36 may communicate the signal to deploy selectively to only robotic structure 20A, which deploys from housing well opening 54A, and robotic structure 20D, which deploys from housing well opening 54D. Robotic structure 20A and robotic structure 20D may then deploy to and around the arm of the user as discussed with reference to FIG. 4B. The robotic structures that deploy from housing well openings 54B and 54C may remain in a retracted state within their respective housing wells.

With reference now to FIG. 5C, if a very thin or small user were to place his or her arm, for instance, over housing 50 and sensing device 36, sensing device 36 may be able to detect that the arm extends roughly from housing well opening 54A to housing well opening 54B. Therefore, sensing device 36 may communicate the signal to deploy selectively to only robotic structure 20A, which extends from housing well opening 54A, and robotic structure 20B, which extends from housing well opening 54B. Robotic structure 20A and robotic structure 20B may then deploy to and around the arm of the user as discussed with reference to FIG. 4B. The robotic structures that deploy from housing well openings 54C and 54D may therefore remain in a retracted state. The user may place his or her arm between housing well openings 54B and 54C, however, or 54C and 54D. Therefore, at least the robotic structures that extend from housing well openings 54B and 54C may contact either the lateral edge of the body part of the user or the medial edge of the body part of the user depending on where the user places his or her body part. In one embodiment, at least the robotic structures that deploy from housing well openings 54B and 54C may include flexible sensors 30 placed around the entire exterior edge 22A of pliable exterior lining 22. This may ensure that the robotic structures may effectively detect physiological conditions of a user whether they approach the body part of the user from the lateral edge or medial edge of the body part.

Figure 6D:
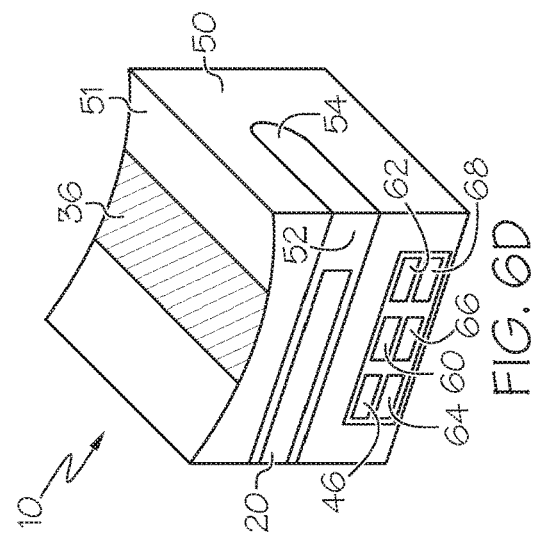
FIG. 6D schematically depicts an illustrative cross-section of the embodiment of FIG. 6B according to one or more embodiments shown or described herein.
Figure 6B:
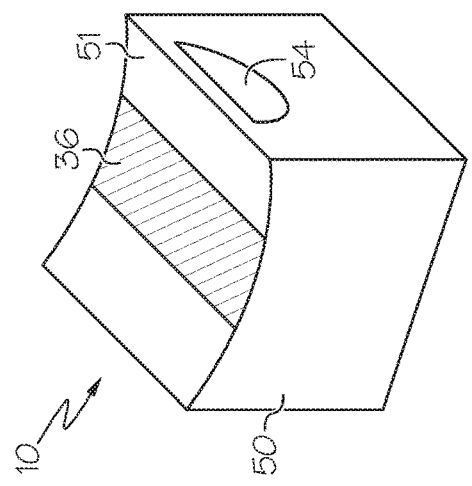
FIG. 6B schematically depicts an embodiment of an extendable biosensing device with a housing well opening at a side surface of a housing according to one or more embodiments shown or described herein.
Figure 6C:
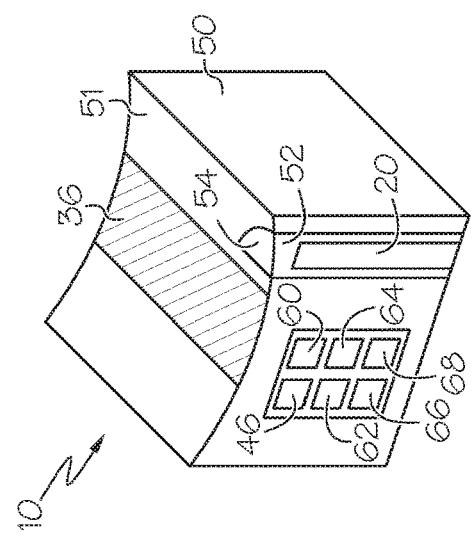
FIG. 6C schematically depicts an illustrative cross-section of the embodiment of FIG. 6A according to one or more embodiments shown or described herein.
Figure 6A:
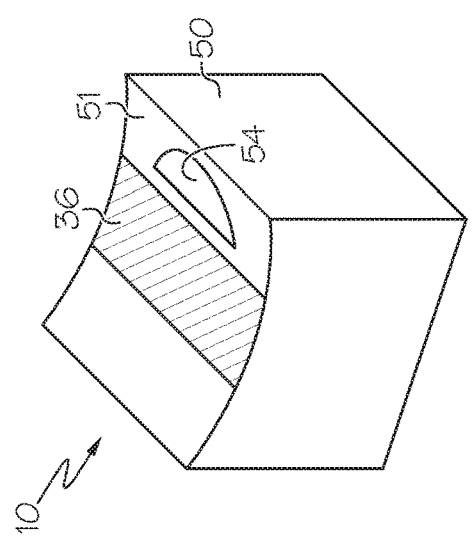
FIG. 6A schematically depicts an embodiment of an extendable biosensing device with a housing well opening at a top surface of a housing according to one or more embodiments shown or described herein.

Referring now to FIGS. 6A-6D, another example configuration of extendable biosensing device 10 is depicted. Extendable biosensing device 10 may include a robotic structure 20. Referring now to FIGS. 6C and 6D, robotic structure 20 may be contained in housing well 52. Housing well 52 may be operatively arranged and sized to both contain robotic structure 20 in a retracted state and to allow passage of robotic structure 20 therethrough as robotic structure 20 begins to extend and deploy. Housing well 52 may include housing well opening 54. Housing well opening 54 may be included on a top surface 51 of housing 50 as depicted in FIG. 6A. In another embodiment, housing well opening 54 may be included on a side surface of housing 50, as depicted in FIG. 6B. Housing well 52 may take different configurations in embodiments depicted in FIGS. 6C and 6D. For instance, in either embodiment, housing well 52 may be predominantly vertical or predominantly horizontal. If housing well 52 were to be predominantly horizontal in a configuration including housing well opening 54 at top surface 51 of housing 50, housing well 52 may include a lateral curvature within housing 50, for instance. In either embodiments depicted in FIG. 6C or 6D, housing well 52 may terminate at different portions of housing 50. Housing well 52 may terminate at a bottom edge of housing 50. In another embodiment, housing well 52 may terminate at the center of housing 50. Robotic structure 20 may be fixedly secured at the bottom of housing well 52, ensuring that robotic structure 20 does not detach from housing 50 when extending or in operation. As extendable biosensing device 10 extends, robotic structure 20 deploys from housing well opening 54 and contacts a body part of a user optimally positioned to receive robotic structure 20.

Figure 6F:
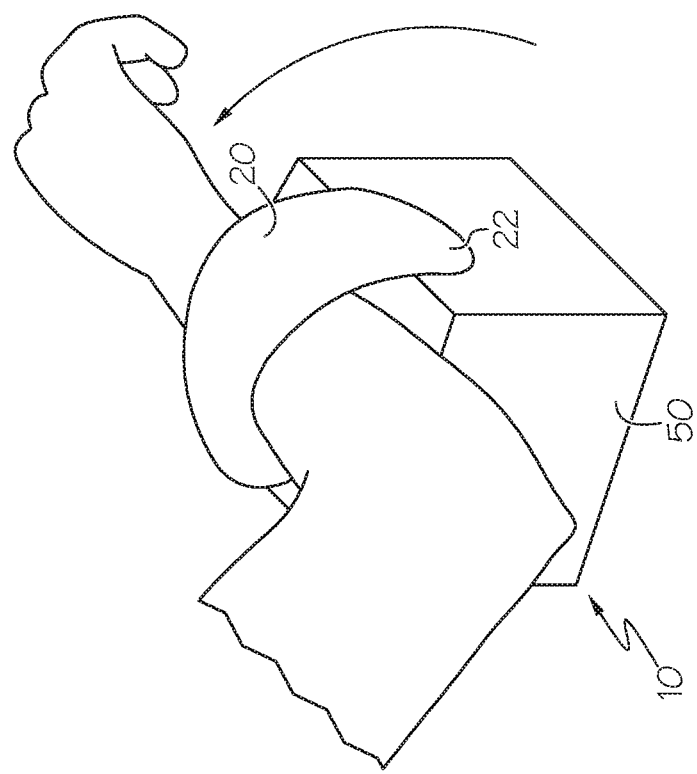
FIG. 6F schematically depicts the embodiment of FIG. 6E with the extendable biosensing device in a deployed state according to one or more embodiments shown or described herein.
Figure 6E:
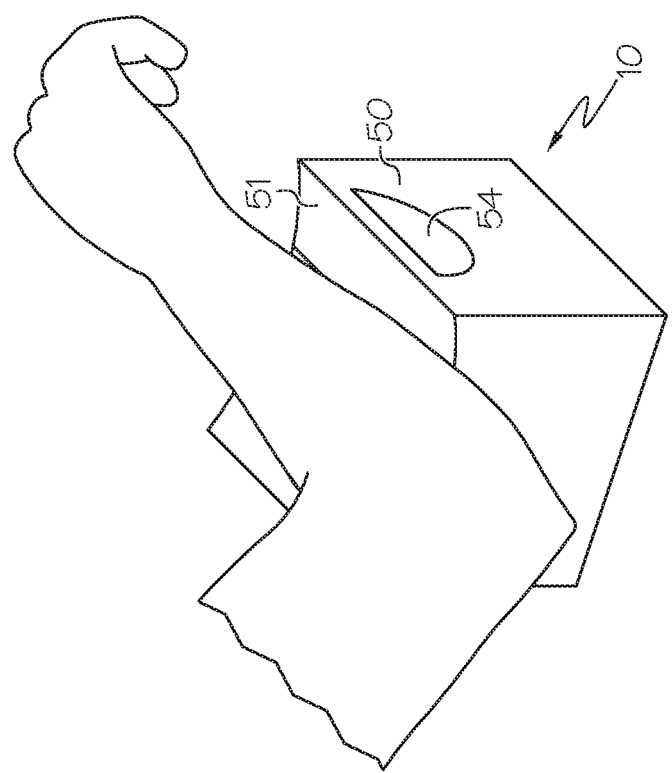
FIG. 6E schematically depicts the embodiment of FIG. 6B with a body part on the extendable biosensing device according to one or more embodiments shown or described herein.

Referring now to FIGS. 6E and 6F, a schematic depiction of examples of the embodiments depicted in FIGS. 6A-6D in relation to a body part of a user is depicted. In FIG. 6E, a user may place his or her arm or other body part on or over sensing device 36. Upon detecting the triggering event, robotic structure 20 extends and deploys. Extendable biosensing device 10, and more specifically, robotic structure 20, may conform to the body part of the user in a spiral shape, as seen in FIG. 6F. Robotic structure 20 may extend around a portion of the circumference of the body part. In another embodiment, robotic structure 20 may extend around the entire circumference of the body part. In yet another embodiment, robotic structure 20 may extend around the circumference of the body part multiple times. The distance robotic structure 20 extends around the body part of the user may depend on the overall length of robotic structure 20, the degree of extension of robotic structure 20, or the size of the body part of the user. Sensing device 36 may be able to detect the width of the body part of the user. Based on this detected width, extendable biosensing device 10 may extend robotic structure 20 only a certain distance. For instance, extendable biosensing device 10 may be calibrated so a certain amount of pneumatic actuation or a certain amount of heating or cooling, for example, of extendable element control 28 is known to result in a certain length of extension of robotic structure 20. Therefore, if it is desirable for robotic structure 20 to make one full revolution or spiral around a body part of a user, biosensing device 10 may only pressurize, heat, cool, or otherwise influence extendable core 24 and/or extendable elements 26 to an amount that correlates with the required distance of extension based on the estimated circumference or width of the body part of the user. Pliable exterior lining 22 may conform to optimally fit a variety of body shapes. Depending on the specific size, shape, and characteristics of the body part, pliable exterior lining 22 may take different shapes or configurations. Pliable exterior lining 22 may mold itself to directly fit or abut the body part. Therefore, there may be no open space between pliable exterior lining 22 and the body part. Robotic structure 20 may be molded to take roughly a certain shape in a deployed state. For instance, if shape-memory alloy were used as extendable elements 26, the shape-memory alloy may be created to remember a distinct shape when it extends, for instance. In one embodiment, that distinct shape may be a spiral configuration. Therefore, robotic structure 20 may be molded to take a certain configuration, assisting pliable exterior lining 22 in directly fitting the body part of the user.

An example of the spiral configuration can be seen in FIG. 6F. Robotic structure 20 may include flexible sensors 30 around the entire circumference of robotic structure 20. In another embodiment, flexible sensors 30 may be placed on portions of exterior edge 22A of pliable exterior lining 22 expected to contact the body part of the user. The spiral configuration of FIG. 6F may restrict the movement of the body part of the user that robotic structure 20 contacts. For this reason, the spiral configuration of robotic structure 20 may be selectively implemented in settings where a user is not likely to need full range of movement. In another embodiment, robotic structure 20 in the spiral configuration may be releasably secured to housing well 52. When a user applies a threshold force to robotic structure 20, robotic structure 20 may unlock and disengage from housing well 52. For instance, if the spiral configuration is implemented in a vehicle, a driver may want to quickly remove his or her arm from biosensing device 10 in an emergency situation. Therefore, by lifting his or her arm with enough force, robotic structure 20 may disengage from housing well 52 and the user may be able to freely move his or her arm. The user may then feed robotic structure 20 back into housing well 52, causing robotic structure 20 to re-engage and again become releasably secured to housing well 52.

Extendable biosensing device 10 may be configured to supply users with real-time readouts or measurements of their certain physiological conditions. Extendable biosensing device 10 may include a display, such as a digital screen or a speaker, for instance. Flexible sensors 30 may collect physiological information and transmit the data to microprocessor 66 for data filtration and analysis. Microprocessor 66 may then instruct the one or more display to provide the user with certain readout information. For example, the screen, speaker, or other display on extendable biosensing device 10 may provide users with an exact measurement of a physiological condition. For instance, extendable biosensing device 10 may inform a user that his or her heartrate is currently 80 beats per minute. In another embodiment, extendable biosensing device 10 may supply a user with information related to the historic or average physiological conditions of the user. For instance, microprocessor 66 of extendable biosensing device 10 may store one or more user profile under each user's name. Each user may upload his or her profile directly through prompts on the digital screen of extendable biosensing device 10 with a button, dial, or other actuator attached to extendable biosensing device 10. Alternatively a user may upload her profile on one or more of her smart devices and wirelessly transmit, via Bluetooth or other communication means, the created profile to a transceiver 60 operatively connected to microprocessor 66 of extendable biosensing device 10. A user may notify extendable biosensing device 10 which particular user is currently using extendable biosensing device 10 through the actuator and display. For instance, a user may scroll through the stored one or more user profile on the display until he or she finds and selects his or her name. Once extendable biosensing device 10 recognizes a particular user, it may then supply the user with current physiological information in relation to his or her past averages. For instance, the display may inform a user that his or her heartrate is 10 beats per minute greater than his or her historical average. In another embodiment, extendable biosensing device 10 may be able to provide users with a diagnosis based on national health data. Microprocessor 66 and transceiver 60 may be able to both upload and download physiological measurements from a cloud storage system for instance. When a user creates her profile, she may provide basic information, such as gender, age, weight, etc. Extendable biosensing device 10 may then be able to collect physiological measurements from similar users stored in the cloud storage system, for instance. Extendable biosensing device 10 may then display information to the user compared to national averages, such as a user's heartrate being a certain percentage faster or slower than similar users throughout the nation. Based on the specific physiological condition being measured and the degree of variance from the national average, extendable biosensing device 10 may inform a user to consult a health professional or seek other treatment.

In another design, extendable biosensing device 10 may be implemented in a customizable mobile transport. The customizable mobile transport may be a self-driving transport that provides users or passengers with a unique variety of goods or services. One particular customizable mobile transport may be a health services customizable mobile transport. A health services customizable mobile transport may pick up a user at selected locations and deliver a user to a doctor, hospital, or other healthcare provider. In another embodiment, the health services customizable mobile transport may provide users with certain medical treatments or supplies. Users may be able to enter the customizable mobile transport to receive or purchase basic medications or medical diagnoses. Therefore, it may be desired to implement extendable biosensing device 10 in a health services customizable mobile transport design. A schematic depiction of an example customizable mobile transport is depicted in FIGS. 7A-7C. The customizable mobile transport 90 may include a biosensing chair 92, as depicted in FIG. 7A. Biosensing chair 92 may include extendable biosensing device 10. Housing 50 of extendable biosensing device 10 may be within or part of biosensing chair 92, as depicted in FIGS. 7A-7C. A user may sit in biosensing chair 92 in mobile transport 90, and rest his or her arm or other body part on sensing device 36. As depicted in FIG. 7C, after sensing device 36 detects the triggering event, extendable biosensing device 10 may deploy as described above with reference to FIGS. 1-6. Extendable biosensing device 10 may supply a user with a readout of his or her physiological conditions on the display included on extendable biosensing device 10 or on another display system included in the mobile transport 90. For instance, extendable biosensing device 10 may wirelessly communicate the measured physiological conditions of a user to built-in digital display screens or audio systems in the mobile transport 90, which then display the readout to the user within the mobile transport.

Figure 8:
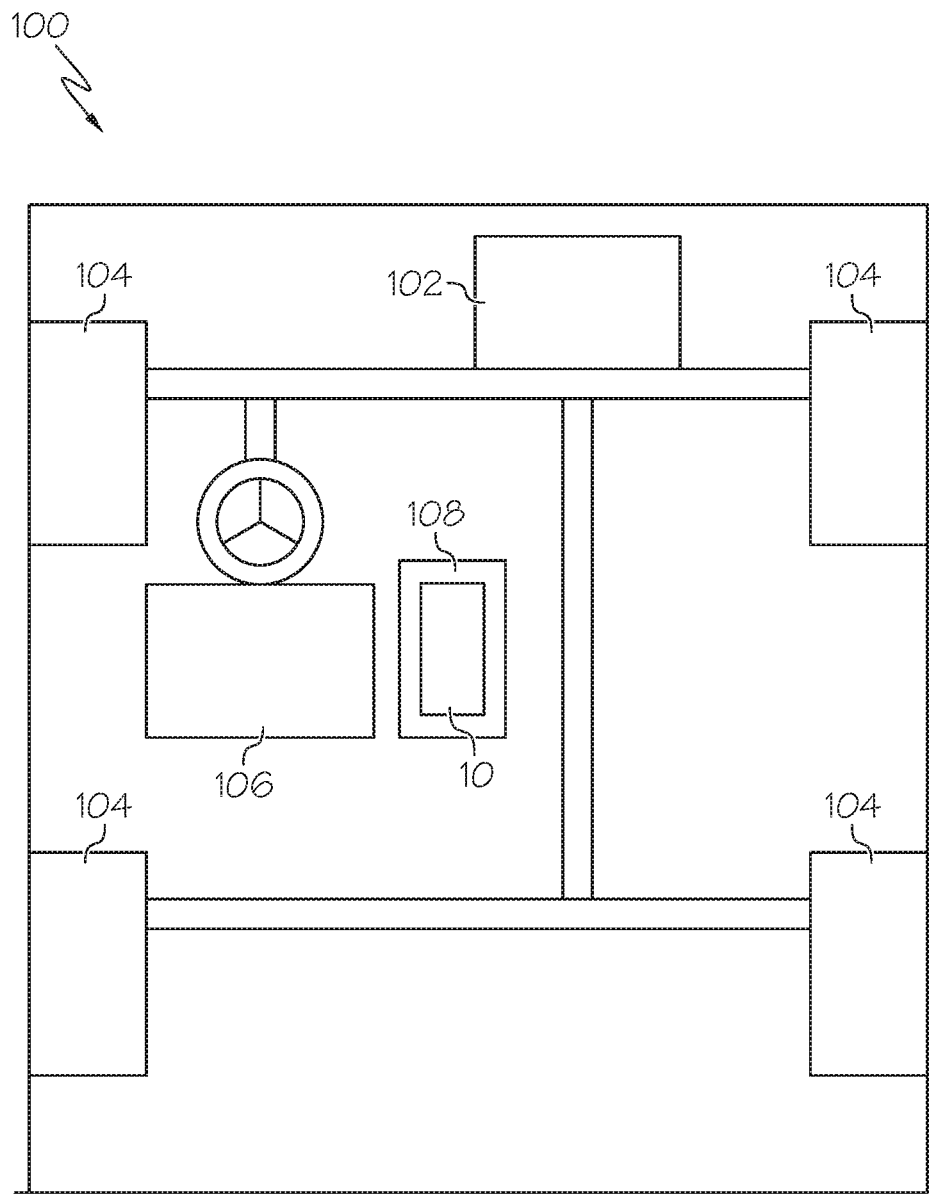
FIG. 8 schematically depicts a vehicle including an extendable biosensing device according to one or more embodiments shown or described herein.

Referring now to FIG. 8, a schematic depiction of an example extendable biosensing device 10 within an example vehicle 100 is depicted. Vehicle 100 may include a motor 102, wheels 104, a seat 106, and any other vehicular components. Extendable biosensing device 10 may be integrated with vehicle 100. Housing 50 of extendable biosensing device 10 may be integrated within any portion of vehicle 100 where a driver or passenger is likely rest a body part. For instance, housing 50 may be within the center console compartment 108 of vehicle 100. Drivers, for example, may comfortably rest one of their arms on the center console compartment 108 while operating vehicle 100, making it a suitable location for extendable biosensing device 10. Sensing device 36 and top surface 51 of housing 50 may be flush with the top surface of center console compartment 108. Extendable biosensing device 10 may operate as described with reference to FIGS. 1-6. In another embodiment housing 50 may be within one or more doors of the vehicle. Sensing device 36 may be flush with the armrest configured on a vehicle door, and robotic structure 20 may deploy from within housing 50 and contact an arm of a user comfortably resting on the armrest. These are merely examples however. Extendable biosensing device 10 may be stored anywhere within vehicle 100 and may be optimally stored to contact a body part of the driver besides the arm.

As briefly discussed above, within vehicle 100, either the partial cuff configuration displayed in FIG. 4E or the spiral configuration displayed in FIG. 6F may be implemented. The partial cuff configuration may easily allow a driver, for instance, to remove his or her arm or other body part from extendable biosensing device 10 in an emergency situation. For instance, when an arm of the driver arm is engaged with extendable biosensing device 10, the driver may not be able to use that arm to control the steering wheel. If an emergency situation arises, the driver may be able to quickly remove his or her arm from the partial cuff to have two hands on the steering wheel. The spiral configuration depicted in FIG. 6F may also be implemented in vehicle 100. If the spiral configuration of extendable biosensing device 10 is implemented to detect physiological conditions of a driver, it may be desired that robotic structure 20 of extendable biosensing device 10 be able to quickly disengage from housing well 52. Extendable biosensing device 10 in either partial cuff configuration, spiral configuration, or any other configuration may also be implemented elsewhere in vehicle 100 to measure physiological conditions of passengers.

Extendable biosensing device 10 may be useful for drivers of vehicle 100. The automatic extension and deployment of extendable biosensing device 10 prevents a driver of vehicle 100 from forgetting to apply a regular vital sign detector to herself. As soon as the driver enters vehicle 100 and places a body part in a position to receive robotic structure 20, extendable biosensing device 10 may deploy to monitor the physiological conditions of the driver. In addition, extendable biosensing device 10 may allow drivers to take precautionary measures before experiencing a health crisis. For instance, a driver, because of the physiological readouts supplied by extendable biosensing device 10, may be able to predict a heart attack, stroke, or any other health crisis before it incapacitates the driver. The driver may then pull over vehicle 100 and call for an ambulance. Extendable biosensing device 10 in vehicle 100 may reduce the likelihood of a driver unknowingly experiencing a health crisis while driving, a situation that puts themselves and others on the road in great danger.

Extendable biosensing device 10 may also be utilized in vehicle 100 to provide mechanical stability and structural support to passengers. For instance, infants and toddlers are often times difficult to safely secure in backseats of vehicles. If a child is not properly sitting in the backseat, the child is far more likely to suffer serious injuries in the event of an automobile accident. Therefore, extendable biosensing device 10 may be implemented in the backseat of vehicle 100. Robotic structure 20 of extendable biosensing device 10 may lightly restrain children, ensuring they securely sit upright in the backseat. In addition, extendable biosensing device 10 may simultaneously detect physiological conditions of the young child, providing parents or adults with useful health information on their children.

What is claimed is:

1. An extendable biosensing device, comprising:
 a housing; and
 a robotic structure, the robotic structure comprising:
  a pliable exterior lining;
  an extendable core; and
  at least one sensor located on or within the pliable exterior lining, the at least one sensor configured to measure a physiological condition of a user,
   wherein the extendable core automatically extends from a retracted state to a deployed state in response to a triggering event,
   wherein: the extendable core, in the retracted state, is concealed within the housing; the extendable core, in the deployed state, is extended from the housing; and the triggering event occurs when a body part of the user is positioned to be measured by the at least one sensor.

2. The extendable biosensing device of claim 1, wherein the at least one sensor is flexible.

3. The extendable biosensing device of claim 2, wherein the extendable core automatically retracts when the triggering event expires.

4. The extendable biosensing device of claim 3, wherein the robotic structure, in the deployed state, is configured to wrap itself around a body part of a user.

5. The extendable biosensing device of claim 4, wherein the robotic structure, in the deployed state, approaches the body part of the user from either a medial edge of the body part or a lateral edge of the body part, wrapping itself around the body part.

6. The extendable biosensing device of claim 4, wherein the robotic structure, in the deployed state, further comprises a first robotic portion and a second robotic portion, the first robotic portion configured to approach the body part of the user from a lateral edge of the body part, and the second robotic portion configured to approach the body part from a medial edge of the body part.

7. The extendable biosensing device of claim 6, wherein a sum of a circumferential distance of the first robotic portion around the body part and a circumferential distance of the second robotic portion around the body part is less than a circumference of the body part.

8. The extendable biosensing device of claim 4, wherein the triggering event is the body part of the user positioned to receive the robotic structure in a deployed state.

9. The extendable biosensing device of claim 8, wherein the extendable biosensing device further comprises a sensing device configured to recognize the triggering event.

10. The extendable biosensing device of claim 9, wherein the sensing device is selected from the group consisting of a visual sensor, a capacitive sensor, a temperature sensor, and a force sensor.

11. The extendable biosensing device of claim 9, wherein the extendable core extends by inflation, the inflation caused by a pneumatic system operatively connected to the extendable core.

12. The extendable biosensing device of claim 9, wherein the extendable core includes an extendable element.

13. The extendable biosensing device of claim 12, wherein the extendable element is an elastomer.

14. The extendable biosensing device of claim 12, wherein the extendable element is a shape-memory alloy.

15. The extendable biosensing device of claim 12, wherein the extendable element is a polymer.

16. The biosensing device of claim 1, wherein:
the robotic structure does not surround a body part of the user when the core is in the retracted state; and
the robotic structure at least partially surrounds the body part of the user when the core is in the deployed state.

17. An extendable biosensing device, comprising:
a robotic structure, the robotic structure comprising:
a pliable exterior lining;
an extendable core; and
at least one flexible sensor located on or within the pliable exterior lining, the at least one flexible sensor configured to measure a physiological condition of a user,
wherein: the extendable core automatically extends from a retracted state to a deployed state in response to a triggering event, and the extendable core automatically retracts when the triggering event expires; the triggering event occurs when a body part of the user is positioned to be measured by the at least one flexible sensor; the extendable core, in the retracted state, is concealed within a housing; the robotic structure, in the deployed state, is extended from the housing and configured to wrap itself around a body part of a user; and the housing which conceals the robotic structure in the retracted state is on or within an interior member of a mobile transport.

18. A vehicle, comprising:

a motor;

two wheels;

a seat; and an extendable biosensing device, the extendable biosensing device further comprising:
a robotic structure, the robotic structure further comprising:
a pliable exterior lining;
an extendable core; and
at least one flexible sensor located on or within the pliable exterior lining, the at least one flexible sensor configured to measure a physiological condition a user,
wherein the extendable core automatically extends from a retracted state to a deployed state in response to a triggering event, and the extendable core automatically retracts when the triggering event expires; the triggering event occurs when a body part of the user is positioned to be measured by the at least one flexible sensor; the extendable core, in the retracted state, is concealed within a housing; and the robotic structure, in the deployed state, is extended from the housing and configured to wrap itself around a body part of a user.

19. The vehicle of claim 18 wherein the housing is on or within an interior portion of the vehicle, the user being able to rest his or her arm on the interior portion when the user operates the vehicle.

20. The vehicle of claim 18, wherein the robotic structure is configured to secure a passenger in a seat of the vehicle.

* * * * *